United States Patent [19]

Martel et al.

[11] 4,328,167

[45] May 4, 1982

[54] PROCESS FOR THE PREPARATION OF OPTICALLY ACTIVE CYANO ALCOHOLS

[75] Inventors: Jacques Martel, Bondy; Jean Tessier, Vincennes; Jean-Pierre DeMoute, Montreuil-sous-Bois, all of France

[73] Assignee: Roussel Uclaf, Paris, France

[21] Appl. No.: 155,753

[22] Filed: Jun. 2, 1980

[30] Foreign Application Priority Data

Jun. 12, 1979 [FR] France ........................... 79 14977

[51] Int. Cl.³ ................................... C07C 121/75
[52] U.S. Cl. .............................. 260/465 F; 260/464; 260/465.6; 546/300; 549/60; 549/65; 549/75; 548/477; 548/513; 548/561; 549/472; 549/479; 549/491
[58] Field of Search ............... 260/465 F, 465.6, 464, 260/326 N, 326.5 R, 347.8; 546/300; 549/75

[56] References Cited

PUBLICATIONS

Huzo et al., Tetrahedron Letters, No. 35, pp. 3045–3048, (1976).
Huzo et al., J. Agric. Food Chem., vol. 25, No. 6, pp. 1385–1394, (1977).

*Primary Examiner*—Dolph H. Torrence
*Attorney, Agent, or Firm*—Hammond & Littell, Weissenberger and Muserlian

[57] ABSTRACT

A novel process for the preparation of optically active alcohols of the formula

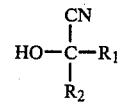

wherein $R_1$ and $R_2$ are individually selected from the group consisting of hydrogen, saturated and unsaturated, optionally substituted aliphatic, cycloaliphatic, aromatic and heterocyclic, with the proviso that at least one of $R_1$ and $R_2$ is other than hydrogen, and $R_1$ and $R_2$ taken together with the carbon atom to which they are attached form a hydrocarbon ring comprising reacting an ester of an optically active alcohol of the formula

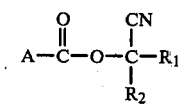

wherein A is the organic radical of a chiral carboxylic acid of the formula

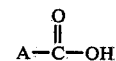

with a boron halide and reacting the resulting mixture with water to obtain the optically active isomer of the alcohol of formula I with the same configuration of the alcohol moiety of the starting ester in high yields without by-products of known processes.

10 Claims, No Drawings

PROCESS FOR THE PREPARATION OF OPTICALLY ACTIVE CYANO ALCOHOLS

STATE OF THE ART

Until now, there has not existed a single process for preparing (S) α-cyano alcohols such as (S) α-cyano-3-phenoxy-benzyl alcohol as the α-cyano alcohols are particularly fragile and can not be prepared by known methods of resolution of the corresponding (R,S) alcohols. One process for the preparation of (S) α-cyano-3-phenoxy-benzyl alcohol is described in published French Pat. No. 2,421,875.

Other pertinent prior art are French Pat. No. 2,352,768, No. 2,396,745 and No. 2,067,854, commonly assigned U.S. Pat. No. 4,133,826 and copending applications Ser. No. 28,994 filed Apr. 11, 1979, now U.S. Pat. No. 4,202,835 and Ser. No. 973,791 filed Dec. 28, 1978.

OBJECTS OF THE INVENTION

It is an object of the invention to provide an improved process for the preparation of optically active α-cyano alcohols in high yields.

This and other objects and advantages of the invention will become obvious from the following detailed description.

THE INVENTION

The novel process of the invention for the preparation of optically active alcohols of the formula

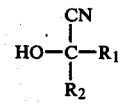

wherein $R_1$ and $R_2$ are individually selected from the group consisting of hydrogen, saturated and unsaturated, optionally substituted aliphatic, cycloaliphatic, aromatic and heterocyclic, with the proviso that at least one of $R_1$ and $R_2$ is other than hydrogen, and $R_1$ and $R_2$ taken together with the carbon atom to which they are attached form a hydrocarbon ring comprises reacting an ester of an optically active alcohol of the formula

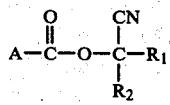

wherein A is the organic radical of a chiral carboxylic acid of the formula

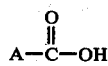

with a boron halide and reacting the resulting mixture with water to obtain the optically active isomer of the alcohol of formula I with the same configuration of the alcohol moiety of the starting ester.

Preferably, $R_2$ is hydrogen or

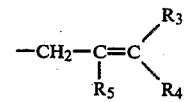

and $R_3$, $R_4$ and $R_5$ are individually selected from the group consisting of hydrogen, methyl and chlorine and $R_1$ is selected from the group consisting of optionally substituted alkenyl, optionally substituted alkynyl, aryl optionally substituted with halogen or methyl and obligatorily substituted with monocyclic arylthio or aryloxy, the latter 2 groups being optionally substituted themselves, monocyclic aryl optionally substituted with at least one member of the group consisting of halogen, alkyl of 1 to 7 carbon atoms, alkenyloxy and alkynyloxy of 2 to 6 carbon atoms, arylalkoxy, phenoxyphenyl, benzylfuryl, phenylthiophenyl, halophenyl and halophenoxyphenyl, monocyclic aryl substituted with

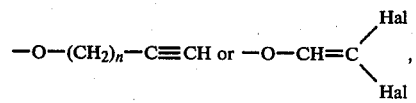

wherein n is 1 to 3 and Hal is a halogen, optionally substituted pyrrolyl, furyl or thienyl optionally substituted with a member of the group consisting of alkyl and alkoxy of 1 to 7 carbon atoms, alkynyl of 2 to 6 carbon atoms, benzyl, thienyl, furylmethyl and halogen, pyridinyl substituted with a monocyclic aryloxy or arylthio optionally substituted with a member of the group consisting of alkyl, alkoxy and alkylthio of 1 to 7 carbon atoms, alkylsulfonyl of 1 to 7 carbon atoms and halogen, optionally substituted cycloalkyl of 3 to 8 carbon atoms, preferably with —C═O, optionally substituted phthalimidomethyl, optionally substituted tetrahydrophthalimidomethyl or

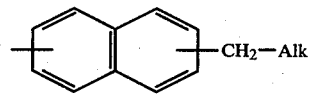

wherein Alk is alkyl of 1 to 7 carbon atoms.

The chiral carboxylic acid of the formula

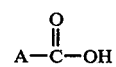

may be an aliphatic carboxylic acid, an aromatic carboxylic acid of one or more rings, an acid of polycyclanic structure, steroid structure or a cyclopropane carboxylic acid.

Examples of specific chiral carboxylic acids whose esters are useful in the process of the invention are 2,2-dimethyl-3-(2,2-dibromovinyl)-cyclopropane-1-carboxylic acids, 2,2-dimethyl-3-(2,2-dichlorovinyl)-cyclopropane-1-carboxylic acids, 2,2-dimethyl-3-(cyclobutylidenemethyl)-cyclopropane-1-carboxylic acids, 2,2-dimethyl-3-(fluorenylidenemethyl)-cyclopropane-1-carboxylic acids, 2,2-dimethyl-3-(2-oxo-3-oxa-cyclopentylidenemethyl)-cyclopropane-1-carboxylic acids, 2,2-dimethyl-3-(2,2-difluorovinyl)-cyclopropane-1-carboxylic acids and 2-(3-chlorophenyl)-2-isopropylacetic acids.

The boron halide may be especially boron tribromide or boron trichloride. The reaction is preferably effected in an organic solvent such as methylene chloride at temperatures of about −40° C. to 0° C., most preferably about −20° C. Preferably, 2 or more moles of the boron halide per mole of ester are used.

While the reaction mechanism has not been completely elucidated, it is certain that the action of water after the reaction with the boron halide is essential for the reaction and to obtain the chiral acid and the optically active alcohol. The optically active alcohols resulting from the process are in a pure state obtained in high yields and the reaction is totally different from the prior art.

The optically active alcohols produced by the process, and especially (S) α-cyano-3-phenoxy-benzyl alcohol, are known to be esterified with acids to produce insecticidal esters inaccessible due to the lack of availability of the (S) alcohol.

The starting esters of optically active α-cyano alcohols may be prepared in very good yields from the esters of the corresponding (R,S) alcohols using a base and a solvent in which the ester of the (S) alcohol is insoluble such as described in Belgium Pat. No. 853,867. The preferred acids are the ones discussed above.

In the following examples there are described several preferred embodiments to illustrate the invention. However, it should be understood that the invention is not intended to be limited to the specific embodiments.

EXAMPLE 1

(S) α-cyano-3-phenoxy-benzyl alcohol 10 ml of a molar solution of boron trichloride in methylene chloride were added dropwise at −40° C. to a mixture of 2 g of (S) α-cyano-3-phenoxy-benzyl 1R, cis 2,2-dimethyl-3-(2,2-dibromovinyl)-cyclopropane-1-carboxylate in 20 ml of methylene chloride and the mixture was stirred at −30° C. for 2 hours. The mixture was poured with stirring into an ice-water mixture and the pH was adjusted to 7 with addition of sodium bicarbonate. The aqueous mixture was extracted with methylene chloride and the organic phase was evaporated to dryness under reduced pressure. The residue was chromatographed over silica gel and was eluted with a 92.5–7.5 benzene-ethyl acetate mixture to obtain 0.640 g of (S) α-cyano-3-phenoxy-benzyl alcohol with a specific rotation of $[\alpha]_D^{20} = -19°$ (c=0.8% in chloroform).

EXAMPLE 2

15 ml of a molar solution of boron trichloride in methylene chloride was added dropwise at −35° C. to a mixture of 3 g of (S) α-cyano-3-phenoxy-benzyl 1R, cis 2,2-dimethyl-3-(2,2-dibromovinyl)-cyclopropane-1-carboxylate in 30 ml of methylene chloride and the mixture was stirred for 2 hours at about −30° C. The mixture was poured with stirring into an ice-water mixture and the aqueous phase was adjusted a pH of 7 by addition of sodium bicarbonate. The mixture was extracted with methylene chloride and the organic phase was evaporated to dryness under reduced pressure. The residue was chromatographed over silica gel and was eluted with a 92.5–7.5 benzene-ethyl acetate mixture to obtain 0.95 g of (S) α-cyano-3-phenoxy-benzyl alcohol.

EXAMPLE 3

250 ml of a solution of 1.6 M of boron trichloride in methylene chloride were slowly added at −35° C. to a solution of 38.5 g of (S) α-cyano-3-phenoxy-benzyl 1R, cis 2,2-dimethyl-3-(2,2-dichlorovinyl)-cyclopropane-1-carboxylate in 385 ml of methylene chloride and the mixture was stirred for 30 minutes and was then poured into an ice-water mixture. The mixture was vigorously stirred for 15 hours and the pH was then adjusted to 7 by addition of sodium bicarbonate. The mixture was extracted with methylene chloride and the organic phase was dried and evaporated to dryness under reduced pressure. The residue was chromatographed over silica gel and was eluted with a 92.5–7.5 benzene-ethyl acetate mixture to obtain 16.9 g of (S) α-cyano-3-phenoxy-benzyl alcohol.

EXAMPLE 4

250 ml of a solution of 1.6 M of boron trichloride in methylene chloride were slowly added at −30° C. to a solution of 50.9 g of (S) α-cyano-3-phenoxy-benzyl 1R, cis 2,2-dimethyl-3-(fluorenylidenemethyl)-cyclopropane-1-carboxylate in 510 ml of methylene chloride and the mixture was stirred for 2 hours at −30° C. and was then poured into a water-ice mixture. The mixture was stirred vigorously for 15 hours and the pH was then adjusted to 7 by sodium bicarbonate addition. The mixture was extracted with methylene chloride and the organic phase was dried and evaporated to dryness under reduced pressure. The residue was chromatographed over silica gel and was eluted with a 92.5–7.5 benzene-ethyl acetate mixture to obtain 9 g of (S) α-cyano-3-phenoxy-benzyl alcohol.

EXAMPLE 5

250 ml of a solution of 1.6 M of boron trichloride in methylene chloride was added slowly at −5° C. to a solution of 25.7 g of (S) α-cyano-3-phenoxy-benzyl 2-(3-chlorophenyl)-2-isopropyl-acetate in 257 ml of methylene chloride and the mixture was stirred for 2 hours at −5° C. and was then treated as in Example 1. The residue was chromatographed over silica gel and was eluted with a 92.5–7.5 benzene-ethyl acetate mixture to obtain 11.8 g of (S) α-cyano-3-phenoxy-benzyl alcohol.

EXAMPLE 6

250 ml of a solution of 1.6 M of boron trichloride in methylene chloride was slowly added at −35° C. to a solution of 34.5 g of (S) α-cyano-3-phenoxy-benzyl 1R, cis 2,2-dimethyl-3-cyclobutylidenemethyl-cyclopropane-1-carboxylate in 345 ml of methylene chloride and the mixture was stirred at −35° C. for 10 minutes and was then treated as in Example 1. The residue was chromatographed over silica gel and was eluted with a 92.5–7.5 benzene-ethyl acetate mixture to obtain 18 g of (S) α-cyano-3-phenoxy-benzyl alcohol.

Various modifications of the process of the invention may be made without departing from the spirit or scope thereof and it should be understood that the invention is intended to be limited only as defined in the appended claims.

We claim:

1. A process for the preparation of optically active alcohols of the formula $$\begin{array}{c} \text{CN} \\ | \\ \text{HO}-\text{C}-\text{R}_1 \\ | \\ \text{R}_2 \end{array} \qquad \text{I}$$

wherein $R_1$ and $R_2$ are individually selected from the group consisting of hydrogen, saturated and unsaturated, optionally substituted aliphatic, cycloaliphatic, aromatic and heterocyclic, with a proviso that at least one of $R_1$ and $R_2$ is other than hydrogen, and $R_1$ and $R_2$ taken together with the carbon atoms to which they are attached form a hydrocarbon ring comprising reacting an ester of an optically active alcohol of the formula $$\begin{array}{c} \text{O} \quad\;\; \text{CN} \\ \| \qquad | \\ \text{A}-\text{C}-\text{O}-\text{C}-\text{R}_1 \\ \qquad\qquad | \\ \qquad\qquad \text{R}_2 \end{array}$$

wherein A is the organic radical of a chiral carboxylic acid of the formula $$\begin{array}{c} \text{O} \\ \| \\ \text{A}-\text{C}-\text{OH} \end{array}$$

with a boron halide and reacting the resulting mixture with water to obtain the optically active isomer of the alcohol of formula I with the same configuration of the alcohol moiety of the starting ester.

2. The process of claim 1 wherein $R_2$ is hydrogen or $$-\text{CH}_2-\underset{\underset{R_5}{|}}{\text{C}}=\text{C}\diagup^{R_3}_{\diagdown R_4}$$

and $R_3$, $R_4$ and $R_5$ are individually selected from the group consisting of hydrogen, methyl and chlorine and $R_1$ is selected from the group consisting of optionally substituted alkenyl, optionally substituted alkynyl, aryl optionally substituted with halogen or methyl and obligatorily substituted with monocyclic arylthio or aryloxy, the latter 2 groups being optionally substituted themselves, monocyclic aryl optionally substituted with at least one member of the group consisting of halogen, alkyl of 1 to 7 carbon atoms, alkenyloxy and alkynyloxy of 2 to 6 carbon atoms, arylalkoxy, phenoxyphenyl, benzylfuryl, phenylthiophenyl, halophenyl and halophenoxyphenyl, monocyclic aryl substituted with $$-\text{O}-(\text{CH}_2)_n-\text{C}\equiv\text{CH or }-\text{O}-\text{CH}=\text{C}\diagup^{\text{Hal}}_{\diagdown \text{Hal}},$$

wherein n is 1 to 3 and Hal is a halogen, optionally substituted pyrrolyl, furyl or thienyl optionally substituted with a member of the group consisting of alkyl and alkoxy of 1 to 7 carbon atoms, alkynyl of 2 to 6 carbon atoms, benzyl, thienyl, furylmethyl and halogen, pyridinyl substituted with a monocyclic aryloxy or arylthio optionally substituted with a member of the group consisting of alkyl, alkoxy and alkylthio of 1 to 7 carbon atoms, alkylsulfonyl of 1 to 7 carbon atoms and halogen, optionally substituted cycloalkyl of 3 to 8 carbon atoms preferably with —C=O, optionally substituted phthalimidomethyl, optionally substituted tetrahydrophthalimidomethyl or

[naphthyl]—CH₂—Alk wherein Alk is alkyl of 1 to 7 carbon atoms.

3. The process of claim 1 wherein the chiral acid is selected from the group consisting of aliphatic carboxylic acids, aromatic carboxylic acids of at least one ring, cyclopropane carboxylic acids, steroid carboxylic acids and polycyclanic carboxylic acids.

4. The process of claim 3 wherein the chiral acid is selected from the group consisting of 2,2-dimethyl-3-(2,2-dibromovinyl)-cyclopropane-1-carboxylic acids, 2,2-dimethyl-3-(2,2-dichlorovinyl)-cyclopropane-1-carboxylic acids, 2,2-dimethyl-3-(cyclobutylidenemethyl)-cyclopropane-1-carboxylic acids, 2,2-dimethyl-3-(fluorenylidenemethyl)-cyclopropane-1-carboxylic acids, 2,2-dimethyl-3-(2-oxo-3-oxa-cyclopentylidenemethyl)-cyclopropane-1-carboxylic acids, 2,2-dimethyl-3-(2,2-difluorovinyl)-cyclopropane-1-carboxylic acids and 2-(3-chlorophenyl)-2-isopropyl-acetic acids.

5. The process of claim 4 wherein the boron halide is boron tribromide.

6. The process of claim 4 wherein the boron halide is boron trichloride.

7. The process of claim 4 wherein the reaction with the boron halide is effected in methylene chloride at $-40°$ to $0°$ C.

8. The process of claim 7 wherein the temperature is about $-20°$ C.

9. The process of claim 1 wherein 2 moles of boron halide are used per mole of ester.

10. A process for the preparation of (S) α-cyano-3-phenoxy-benzyl alcohol comprising reacting an ester of (S) α-cyano-3-phenoxy-benzyl alcohol of the formula $$\begin{array}{c} \text{O} \quad\;\; \text{CN} \\ \| \qquad | \\ \text{A}-\text{C}-\text{O}-\text{CH}-[\text{phenyl-O-phenyl}] \\ \text{(S)} \end{array}$$

wherein A is selected from the group consisting of 2,2-dimethyl-3-(2,2-dibromovinyl)-cyclopropane-1-carboxylic acids, 2,2-dimethyl-3-(2,2-dichlorovinyl)-cyclopropane-1-carboxylic acids, 2,2-dimethyl-3-(cyclobutylidenemethyl)-cyclopropane-1-carboxylic acids, 2,2-dimethyl-3-(fluorenylidene-methyl)-cyclopropane-1-carboxylic acids, 2,2-dimethyl-3-(2-oxo-3-oxa-cyclopentylidenemethyl)-cyclopropane-1-carboxylic acids, 2,2-dimethyl-3-(2,2-difluorovinyl)-cyclopropane-1-carboxylic acids and 2-(3-chlorophenyl)-2-isopropylacetic acids with at least two moles of a boron halide selected from the group consisting of boron trichloride and boron tribromide in an organic solvent and reacting the resulting mixture with water to obtain (S) α-cyano-3-phenoxy-benzyl alcohol.

* * * * *

UNITED STATES PATENT AND TRADEMARK OFFICE
CERTIFICATE OF CORRECTION

PATENT NO. : 4,328,167
DATED : May 4, 1982
INVENTOR(S) : JACQUES MARTEL ET AL.

It is certified that error appears in the above—identified patent and that said Letters Patent is hereby corrected as shown below:

Title page [75]: The name of the third inventor should read

-- Jean-Pierre Demoute --.

Signed and Sealed this

Fifth Day of October 1982

[SEAL]

Attest:

GERALD J. MOSSINGHOFF

Attesting Officer     Commissioner of Patents and Trademarks